(12) United States Patent
Green et al.

(10) Patent No.: US 9,573,873 B2
(45) Date of Patent: Feb. 21, 2017

(54) CATALYTIC METHOD FOR DIBENZOCYCLOHEPTANE SYNTHESIS AND ALLOCOLCHICINOID SYNTHESIS

(71) Applicant: UNIVERSITY OF WINDSOR, Windsor (CA)

(72) Inventors: James Green, Windsor (CA); Mariam Mehdi, Windsor (CA); Sinisa Djurdjevic, Windsor (CA)

(*) Notice: Subject to any disclaimer, the term of this patent is extended or adjusted under 35 U.S.C. 154(b) by 82 days.

(21) Appl. No.: 14/728,424

(22) Filed: Jun. 2, 2015

(65) Prior Publication Data

US 2015/0344411 A1  Dec. 3, 2015

Related U.S. Application Data

(60) Provisional application No. 62/007,106, filed on Jun. 3, 2014.

(51) Int. Cl.

| | |
|---|---|
| C07C 45/68 | (2006.01) |
| C07C 49/255 | (2006.01) |
| C07C 233/52 | (2006.01) |
| C07C 45/65 | (2006.01) |
| C07C 227/04 | (2006.01) |
| C07C 213/02 | (2006.01) |
| C07C 67/343 | (2006.01) |
| C07C 67/313 | (2006.01) |
| C07C 231/12 | (2006.01) |
| C07C 67/333 | (2006.01) |
| C07C 41/30 | (2006.01) |
| C07C 41/18 | (2006.01) |
| C07D 317/54 | (2006.01) |
| C07D 317/70 | (2006.01) |
| C07C 43/23 | (2006.01) |
| C07C 43/295 | (2006.01) |
| C07C 233/23 | (2006.01) |
| C07C 247/14 | (2006.01) |
| C07C 69/94 | (2006.01) |
| C07C 49/755 | (2006.01) |
| C07C 49/84 | (2006.01) |

(52) U.S. Cl.
CPC .............. *C07C 49/255* (2013.01); *C07C 41/18* (2013.01); *C07C 41/30* (2013.01); *C07C 43/23* (2013.01); *C07C 43/295* (2013.01); *C07C 45/65* (2013.01); *C07C 49/755* (2013.01); *C07C 49/84* (2013.01); *C07C 67/313* (2013.01); *C07C 67/333* (2013.01); *C07C 67/343* (2013.01); *C07C 69/94* (2013.01); *C07C 213/02* (2013.01); *C07C 227/04* (2013.01); *C07C 231/12* (2013.01); *C07C 233/23* (2013.01); *C07C 233/52* (2013.01); *C07C 247/14* (2013.01); *C07D 317/54* (2013.01); *C07D 317/70* (2013.01); *C07C 2103/32* (2013.01)

(58) Field of Classification Search
USPC .......................................... 514/646, 647, 656
See application file for complete search history.

(56) References Cited

PUBLICATIONS

Mariam; Thesis: Part I: Synthesis of a ring modified allocolchicinoids via Lewis acid catalyzed conjugate addition reactions; Part II: Preparation of benzocycloheptadienynol-Co (CO)6 complexes; Apr. 2016.*
Amit, J. et al., "Lateral Lithiation-Initiated Annulations in the Synthesis of 1-Oxygenated Carbazole Alkaloids and a Cycloheptacarbazole", Synlett, 23.12 (2012):1769-1774.
Larocque, K. et al., "Novel Analogue of Colchicine Induces Selective Pro-death Autophagy and Necrosis in Human Cancer Cells", PLOS One, 9.1 (2014):e87064.
Djurdjevic, S et al. "Intramolecular Nicholas Reactions in the Synthesis of Dibenzocycloheptanes. Synthesis of Allocolchicine NSC 51046 and Analogues and the Formal Synthesis of (−)-Allocolchicine ", J. Org. Chem., 75 (2010):8241-8251.
Larocque, K. et al., "Novel Analogue of Colchicine Induces Selectice Pro-death Autophagy and Necrosis in Human Cancer Cells", PLOS One, 9.1 (2014):1-10.
Djurdjevic, S et al. "Intramolecular Nicholas Reactions in the Synthesis of Dibenzocycloheptanes. Synthesis of Allocolchicine NSC 51046 . . . ", J. Org. Chem., 75 (2010):8241-8251.

* cited by examiner

*Primary Examiner* — Pancham Bakshi

(57) ABSTRACT

In a non-limiting embodiment, there is provided a compound of formula (I), which may permit for a method or use in treating or preventing a cancer, such as pancreatic cancer or leukemia. In one embodiment, there is also provide a method of preparing a compound of formula (Ia), the method including conducting a cyclization reaction of a compound of formula (III) to obtain a compound of formula (IV), wherein conducting the cyclization reaction comprises conducting a Michael reaction in the presence of a Lewis acid.

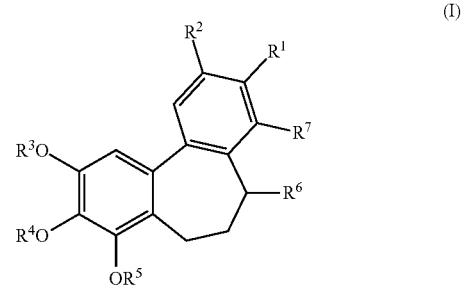

(I)

9 Claims, 3 Drawing Sheets

Scheme 1

Scheme 2

Scheme 3

Scheme 4

Scheme 5

Scheme 6

CATALYTIC METHOD FOR DIBENZOCYCLOHEPTANE SYNTHESIS AND ALLOCOLCHICINOID SYNTHESIS

RELATED APPLICATIONS

The applicant claims the benefit of 35 U.S.C. 119(e) to U.S. Provisional Patent Application Ser. No. 62/007,106 filed on Jun. 3, 2014.

SCOPE OF THE INVENTION

The present invention provides for methods for the synthesis or production of cycloheptane-containing compounds.

BACKGROUND OF THE INVENTION

The allocolchicinoids, or allocolchicines (the terms hereafter used interchangeably), are a well-recognized series of natural products and natural product derivatives based on a dibenzocycloheptane ring system, and which inevitably possess a 9,10,11-trialkoxy substitution pattern in the A ring. Many of the individual compounds of this class are known to have antitumor properties against a variety of cancer cell lines. Unfortunately, these compounds tend to be cardiotoxic, which apparently renders them inapplicable for cancer treatment. For example, ZD 6126 (N-Acetylcolchicinol dihydrogen phosphate) failed in Phase 2 clinical testing because of this cardiotoxicity.

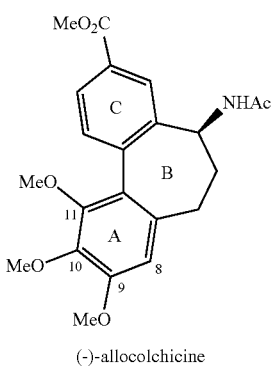

(-)-allocolchicine

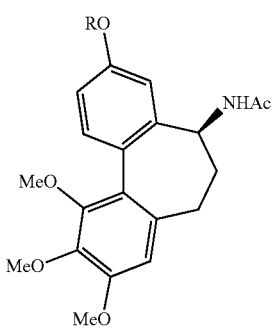

R = Me, NSC 51046
R = H, (-)-N-acetylcolchicinol
R = P(O)(OH)$_2$, ZD 6126

-continued

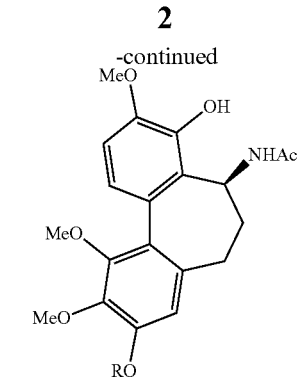

R = Me, (-)-androbiphenyline
R = H, (-)-colchibeiphenyline

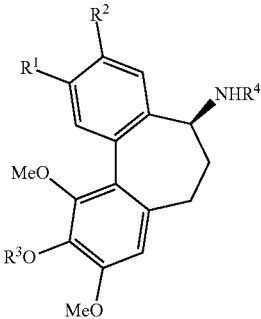

$R^1$ = OH, $R^2$ = OMe, $R^3$ = H, $R^4$ = Me (-)-jerulsalemine
$R^1$ = CO$_2$Me, $R^2$ = OH, $R^3$ = Me, $R^4$ = Ac (-)-salimine

SUMMARY OF THE INVENTION

One possible non-limiting object of the present invention is to provide a method for dibenzocycloheptane Synthesis and allocolchicinoid synthesis which may be catalytic, and which may result in synthesis of compounds of formulae 1 (GREEN1), 14 (GREEN2), 15 (GREEN3), and 16 (GREEN4).

Another possible non-limiting object of the present invention is to provide compounds which may not be cardiotoxic, and/or may have a mechanism of action against pancreatic cancer and leukemia cell lines that is distinguishable from conventional allocolinoids, and which preferably involves pro-death autophagy.

Yet another possible non-limiting object of the present invention is to provide compounds of formulae 1, 14, 15 and/or 16 which are synthetic origin allocolchicinoid with the 8,9,10-trimethoxy-substitution pattern.

Yet another possible non-limiting object of the present invention is to provide a synthesis regime which may simplify and render more efficient the construction of dibenzocycloheptanes that are central to the synthesis of antitumor allocolchicines.

Yet another possible non-limiting object of the present invention is to provide compounds which may possess ring construction which is distinguishable in its chemical nature compared to other known technologies.

Yet another possible non-limiting object of the present invention is to provide a compound which may possess a ring allowing pattern functionalization that are not readily approached by known technologies.

In one aspect, the present invention provides a compound of formula (I):

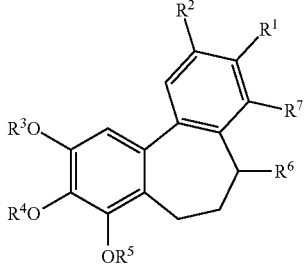

(I)

wherein: $R^1$ and $R^2$ are independently of each other H, OH, OR', C(O)OR', OP(O)(OH)$_2$ or a halogen atom, or $R^1$ and $R^2$ together with adjacent phenyl carbon atoms form a ring structure selected from the group consisting of cycloalkyl, cycloalkenyl, heterocycloalkyl or heterocycloalkenyl having one or more of N, O and S, aryl and heteroaryl having one or more of N, O and S, wherein the ring structure is optionally substituted; $R^3$ to $R^5$ are independently of each other H or R'; $R^6$ is R", NHR", O, OH or N$_3$; $R^7$ is H, OH or OR'; R' is optionally substituted aryl, optionally substituted alkyl, optionally substituted alkenyl or optionally substituted alkynyl; and R" is optionally substituted aryl, optionally substituted alkyl, optionally substituted alkenyl, optionally substituted alkynyl or optionally substituted acyl, or a salt, enantiomer or derivative thereof.

In another aspect, the present invention provides a compound of formula (II):

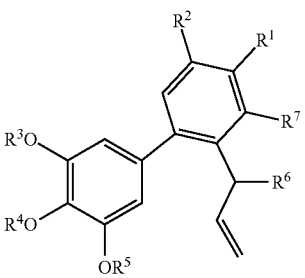

(II)

wherein: $R^1$ and $R^2$ are independently of each other H, OH, OR', C(O)OR', OP(O)(OH)$_2$ or a halogen atom, or $R^1$ and $R^2$ together with adjacent phenyl carbon atoms form a ring structure selected from the group consisting of cycloalkyl, cycloalkenyl, heterocycloalkyl or heterocycloalkenyl having one or more of N, O and S, aryl and heteroaryl having one or more of N, O and S, wherein the ring structure is optionally substituted; $R^3$ to $R^5$ are independently of each other H or R'; $R^6$ is O or OH; $R^7$ is H, OH or OR'; and R' is optionally substituted aryl, optionally substituted alkyl, optionally substituted alkenyl or optionally substituted alkynyl, or a salt, enantiomer or derivative thereof.

In yet another aspect, the present invention provides a method of producing a compound of formula (Ia), or a salt, enantiomer or derivative thereof:

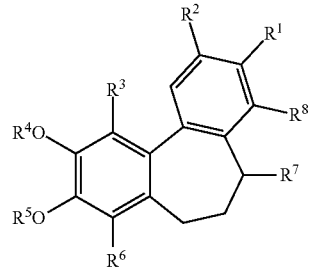

(Ia)

wherein: $R^1$ and $R^2$ are independently of each other H, OH, OR', C(O)OR', OP(O)(OH)$_2$ or a halogen atom, or $R^1$ and $R^2$ together with adjacent phenyl carbon atoms form a ring structure selected from the group consisting of cycloalkyl, cycloalkenyl, heterocycloalkyl or heterocycloalkenyl having one or more of N, O and S, aryl and heteroaryl having one or more of N, O and S, wherein the ring structure is optionally substituted; $R^3$, $R^6$ and $R^8$ are independently of each other H, OH or OR', wherein at least one of $R^3$ and $R^6$ is OR'; $R^4$ and $R^5$ are independently of each other H or R'; $R^7$ is R", NHR", O, OH or N$_3$; R' is optionally substituted aryl, optionally substituted alkyl, optionally substituted alkenyl or optionally substituted alkynyl; and R" is optionally substituted aryl, optionally substituted alkyl, optionally substituted alkenyl, optionally substituted alkynyl or optionally substituted acyl, the method comprising conducting a cyclization reaction of a compound of formula (III):

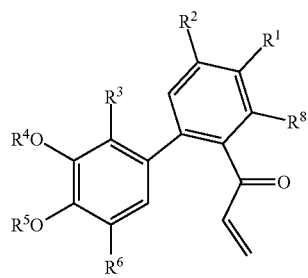

(III)

to obtain a compound of formula (IV):

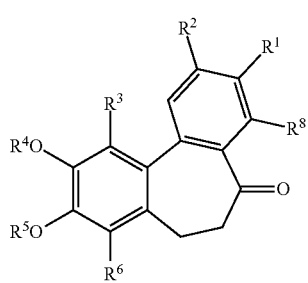

(IV)

wherein $R^1$ to $R^6$ and $R^8$ are as defined for the compound of formula (Ia), and wherein said conducting the cyclization reaction comprises conducting a Michael reaction in the presence of a Lewis acid.

In yet another aspect, the present invention provides a method of treating or preventing a cancer, the method comprising administering a therapeutically effective amount of the compound of formula (I) to a patient. In one embodiment, the cancer is pancreatic cancer or leukemia.

In yet another aspect, the present invention provides a pharmaceutical composition for treating or preventing a cancer, the composition comprising the compound of formula (I) and a pharmaceutically acceptable excipient.

In yet another aspect, the present invention provides use of the compound of formula (I) for treating or preventing a cancer.

In yet another aspect, the present invention provides use of the compound of formula (I) for the manufacture of a medicament for treating or preventing a cancer.

In one embodiment, $R^1$ is H, OR', C(O)OR' or F and $R^2$ is H, OR' or C(O)OR', or $R^1$ and $R^2$ together with adjacent phenyl carbon atoms form heterocycloalkenyl or heteroaryl having one or more of N, O and S, and R' is $C_1$-$C_4$ alkyl or benzyl. In one embodiment, $R^6$ is NHR" and $R^7$ is H, and R" is $C_1$-$C_4$ alkyl or acetyl. In one embodiment, $R^1$ and $R^2$ are independently of each other H, OR' or C(O)OR', and $R^3$ to $R^5$ are R', and R' is $C_1$-$C_4$ alkyl.

In one embodiment, the compound of formula (I) is

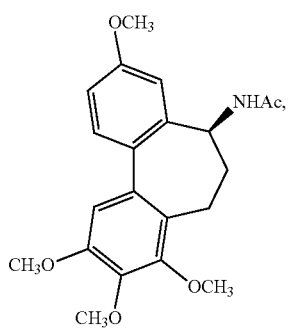

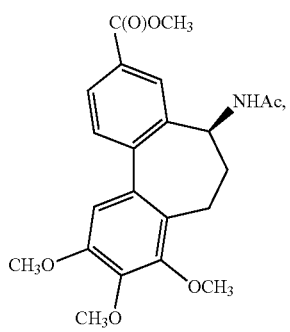

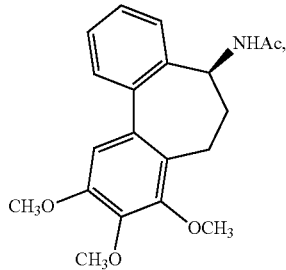

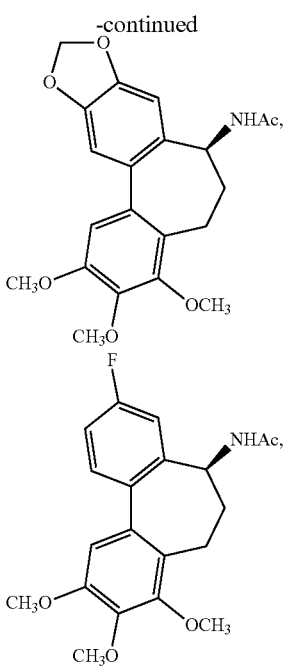

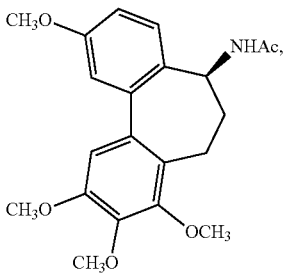

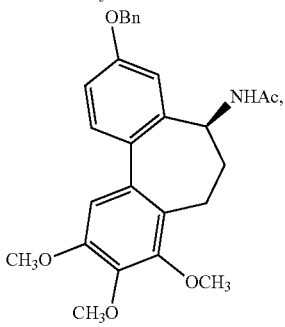

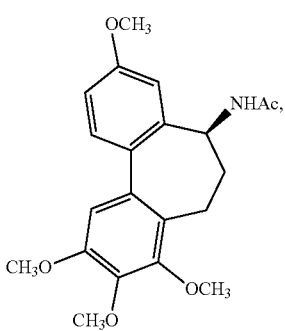

or a salt or derivative thereof, wherein Ac is C(O)CH₃ and Bn is benzyl.

In one embodiment, the compound of formula (I) is

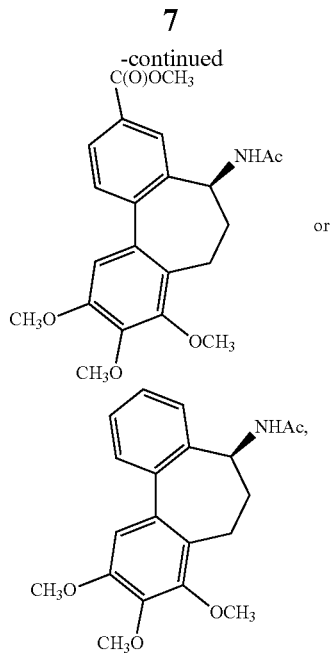
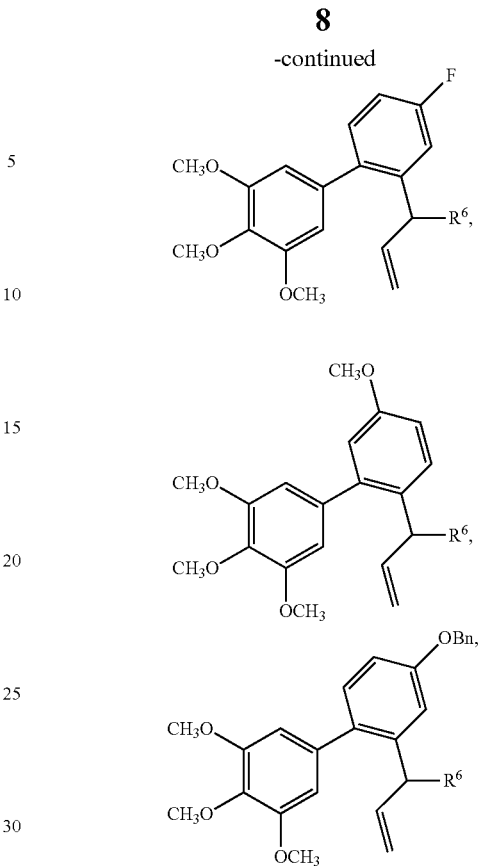
or a salt or derivative thereof, wherein Ac is C(O)CH₃.
In one embodiment, the compound of formula (II) is
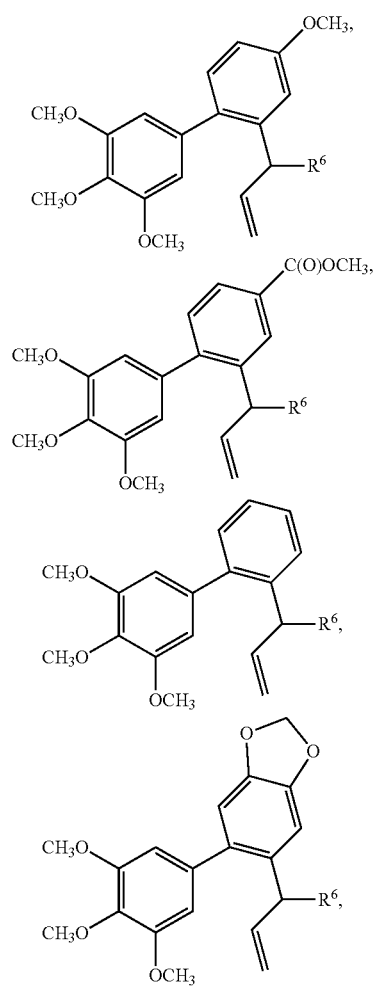
or a salt, enantiomer or derivative thereof, wherein Bn is benzyl, and wherein $R^6$ is as defined for the compound of formula (II).
In one embodiment, the compound of formula (II) is
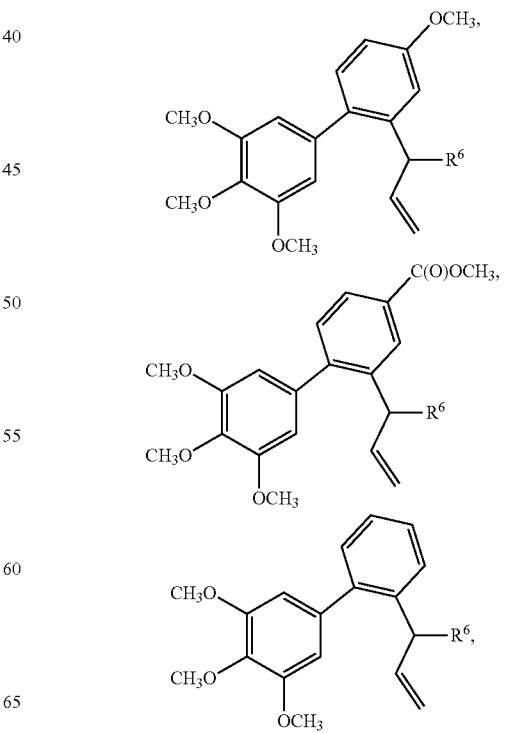

or a salt, enantiomer or derivative thereof, wherein $R^6$ is as defined for the compound of formula (II).

In one embodiment, said conducting the Michael reaction comprises preparing a mixture containing the compound of formula (III), the Lewis acid and a solvent, and optionally refluxing the mixture. It is to be appreciated that the solvent is not particularly limited, and may include one or more of chloroform, dichloromethane, nitrobenzene, acetonitrile, benzene, hexane, cyclohexane, toluene, chloroform, tetrahydrofuran, dimethylformamide and dimethyl sulfoxide. In one embodiment, the Lewis acid comprises one or more of $AlCl_3$, $AuCl_3$, $(CH_3)_2SAuCl$, $AgBF_4$, $FeCl_3$, $InCl_3$, $GaCl_3$, $SnCl_4$, $BF_3$—$O(CH_2CH_3)_2$ and trimethylsilyl trifluoromethanesulfonate. Preferably, the Lewis acid is selected to operate as a Lewis acid catalyst in said Michael reaction.

In one embodiment where $R^3$ is OR' and $R^6$ is H, the Lewis acid preferably includes $GaCl_3$ or $AlCl_3$ preferably in an amount between 1 mol % and 800 mol % with respect to an amount of the compound of formula (III). In another embodiment where $R^3$ is H and $R^6$ is OR', the Lewis acid preferably includes $BF_3$—$O(CH_2CH_3)_2$ preferably in an amount between 1 mol % to 300 mol % with respect to an amount of the compound of formula (III).

In one embodiment, the compound of formula (III) is obtained by reacting a compound of formula (V) with vinylmagnesium halide:

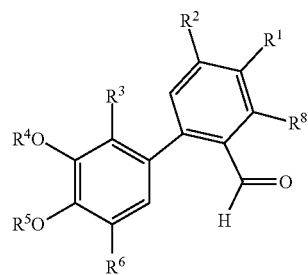

(V)

to obtain a compound of formula (VI):

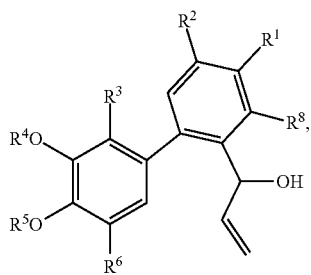

(VI)

and oxidizing the compound of formula (VI) to obtain the compound of formula (III), wherein $R^1$ to $R^6$ and $R^8$ are as defined for the compound of formula (Ia).

In one embodiment, the vinylmagneisum halide is a Grignard reagent. In one embodiment, the vinylmagneisum halide includes vinylmagnesium chloride, vinylmagnesium bromide or vinylmagnesium iodide, or preferably vinylmagnesium bromide. In one embodiment, said reacting the compound of formula (V) is performed in a solvent which preferably includes diethyl ether or tetrahydrofuran, preferably in an inert atmosphere, such as, but not limited to, a nitrogen or argon atmosphere.

Preferably, said oxidizing the compound of formula (VI) is conducted in the presence of $MnO_2$ or tetrapropylammonium perruthenate and N-Methylmorpholine N-oxide.

In one embodiment, the compound of formula (V) is obtained by conducting a Suzuki-Miyaura coupling reaction between compounds of formulas (VII) and (VIII):

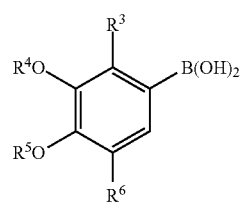

(VII)

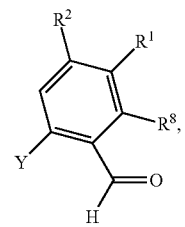

(VIII)

wherein $R^1$ to $R^6$ and $R^8$ are as defined in respect of the compound of formula (Ia), and Y is a halogen atom. In one embodiment, Y is F, Cl, Br or I, or preferably Br.

In one embodiment, said conducting the Suzuki-Miyaura coupling reaction includes preparing a mixture containing the compounds of formulas (VII) and (VIII), a base, a solvent and a catalyst, and optionally refluxing the mixture. The catalyst is preferably a palladium or nickel based catalyst, such as, but not limited to, tetrakis(triphenylphosphine)palladium(0) $(Pd(PPh_3)_4)$, [1,1'-bis(diphenylphosphino)ferrocene]dichloronickel(II) $(NiCl_2(dppf))$, bis(triphenylphosphine)nickel(II) chloride or dichloro[1,3-bis(diphenylphosphino)propane]nickel $(NiCl_2(dppp))$, or more preferably, $Pd(PPh_3)_4$. In one embodiment, the solvent includes one or more of water, dimethyl ether, toluene, tetrahydrofuran, dioxane and dimethylformamide, preferably water and dimethyl ether. In one embodiment, the base includes sodium hydroxide (NaOH), triethylamine ($Et_3N$), sodium carbonate ($Na_2CO_3$), potassium carbonate ($K_2CO_3$), cesium carbonate ($Cs_2CO_3$), tripotassium phosphate ($K_3PO_4$), potassium tert-butoxide (KOtBu) or potassium fluoride (KF), or preferably $K_2CO_3$. In one embodiment, the mixture further includes a promoter, such as, but not limited to, lithium chloride (LiCl).

It is to be appreciated that while the compound of formula (VII) is shown as including two hydroxyls bonded to a boron atom, the boron atom may in the alternative include moieties other than the two hydroxyls, provided that such alternative moieties do not significantly affect the Suzuki-Miyaura coupling reaction with the compound of formula (VIII). Such alternative moieties may include H, alkyl, aryl, alkoxy or a halogen atom, or together with the boron atom may form heterocycloalkyl, heterocycloalkenyl or heteroaryl.

In one embodiment, the method further comprises reducing the compound of formula (IV) with 2-(3-nitrophenyl)-1,3,2-dioxaborolane-4R,5R-dicarboxylic acid ($TARB$-$NO_2$) to obtain a compound of formula (IX):

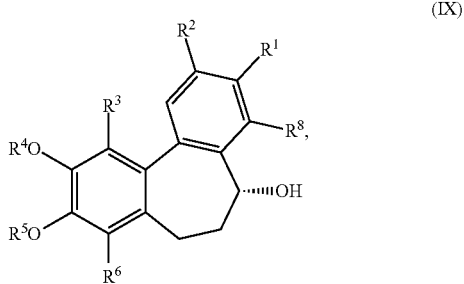

(IX)

reacting the compound of formula (IX) with an azide compound to obtain a compound of formula (X):

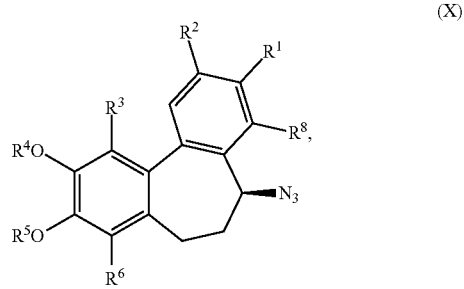

(X)

reducing the compound of formula (X) with hydrogen and a Lindlar catalyst to obtain a compound of formula (XI):

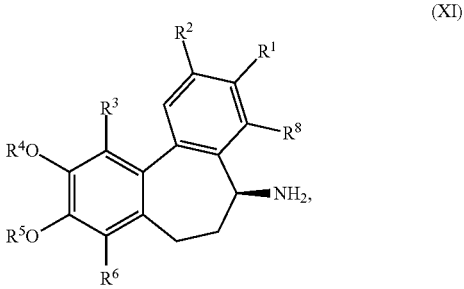

(XI)

and reacting the compound of formula (XI) with an acid anhydride compound to obtain the compound of formula (Ia), wherein $R^7$ is NHC(O)R''', R''' being alkyl, and wherein $R^1$ to $R^6$ and $R^8$ are as defined in respect of the compound of formula (Ia). Preferably, the compound of formula (Ia) as obtained from the aforementioned embodiment has stereochemical configuration of the ring carbon atom bonded to $R^7$ identical to that of the compound of formula (XI).

In one embodiment, said reducing the compound of formula (IV) comprises preparing a mixture containing the compound of formulas (IV), TARB-NO$_2$, at least one compound selected from the group consisting of LiBH$_4$, NaBH$_4$ and KBH$_4$ and a solvent. Preferably, the at least one compound includes LiBH4. The solvent is not particularly limited, and may include one or more of tetrahydrofuran, ethyl acetate, dimethylformamide, acetonitrile, dimethyl sulfoxide, or preferably tetrahydrofuran.

In one embodiment, the azide compound includes a zinc azide/bispyridine complex. In one embodiment, said react-ing the compound of formula (IX) includes preparing a mixture having the compound (IX), the zinc azide/bispyridine complex, diisopropyl azodicarboxylate, triphenylphosphine and a solvent. The solvent is not particularly limited, and may include one or more of hexane, benzene, toluene, chloroform, diethyl ether and dichloromethane, or preferably toluene.

In one embodiment, the Lindlar catalyst comprises palladium deposited on calcium carbonate, and which is poisoned with lead or sulphur. In one embodiment, reacting the compound of formula (XI) with the acid anhydride compound is conducted in a solvent comprising pyridine. In one embodiment, the acid anhydride compound is acetic anhydride, and the compound of formula (Ia) includes NHC(O)CH$_3$ as $R^7$. It is to be appreciated that the compound of formula (Ia) with different $R^7$ may be obtained by modifying or substituting the reactants or reagents for reacting with the compounds of formulas (IV) and (IX) to (XI). In a non-limiting example, the acid anhydride compound may be modified to include propionic anhydride to prepare the compound of formula (Ia) where $R^7$ is NHC(O)CH$_2$CH$_3$.

In one embodiment, the cancer may be caused by proliferation of malignant neoplastic cells, such as tumors, neoplasms, carcinomas, sarcomas, leukemias or lymphomas. For example, the cancer includes, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. The cancer may also include cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer or pituitary cancer. The cancer may further include colon carcinoma, familiary adenomatous polyposis carcinoma and hereditary non-polyposis colorectal cancer, melanoma, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In one embodiment, the halogen atom is F, Cl, Br, I or At.

In one embodiment, the alkyl includes a linear or branched-chain saturated hydrocarbyl substituent. In one embodiment, the alkyl include from one to twelve carbon atoms, preferably from one to six carbon atoms, or more preferably from one to four carbon atoms. In one embodiment, the alkyl includes one or more carbon atoms, independently of each other, substituted with one or more of same or different substituents. Non-limiting examples of the alkyl include methyl, ethyl, propyl (including n-propyl and isopropyl), butyl (including n-butyl, isobutyl, sec-butyl and tert-butyl), pentyl, isoamyl and hexyl.

In one embodiment, the alkenyl includes a straight or branched hydrocarbon chain containing two to twelve carbon atoms, and which has one or more double bonds. In one embodiment, the alkenyl includes one or more carbon atoms, independently of each other, substituted with one or more of same or different substituents. Non-limiting examples of the alkenyl include allyl, propenyl, 2-butenyl, 3-hexenyl and 3-octenyl. One of the double bond carbons may optionally be the point of attachment of the alkenyl.

In one embodiment, the alkynyl includes a straight or branched hydrocarbon chain containing two to twelve carbon atoms, and which has one or more triple bonds. In one embodiment, the alkynyl includes one or more carbon atoms, independently of each other, substituted with one or more of same or different substituents. Non-limiting examples of the alkynyl include ethynyl, propargyl, and 3-hexynyl. One of the triple bond carbons may optionally be the point of attachment of the alkynyl.

In one embodiment, the cycloalkyl includes a saturated cyclic, bicyclic, tricyclic or polycyclic hydrocarbon group, preferably having three to twelve carbon atoms. In one embodiment, the cycloalkyl includes one or more ring carbon atoms, independently of each other, substituted with one or more of same or different substituents. In one embodiment, the cycloalkyl contains fused rings sharing a common carbon atom. Non-limiting examples of the cycloalkyl include cyclopropyl, cyclohexyl, methylcyclohexyl, adamantyl and norbornyl.

In one embodiment, the cycloalkenyl includes a partially unsaturated, nonaromatic, cyclic, bicyclic, tricyclic or polycyclic hydrocarbon group, preferably having five to twelve carbon atoms, or more preferably five to eight carbons. The unsaturated carbon may optionally be the point of attachment of the cycloalkenyl. In one embodiment, the cycloalkenyl includes one or more ring carbon atoms, independently of each other, substituted with one or more of same or different substituents. In one embodiment, the cycloalkenyl contains fused rings sharing a common carbon atom. Non-limiting examples of the cycloalkenyl include cyclohexenyl, cyclohexadienyl and norbornenyl.

In one embodiment, the heterocycloalkyl includes a saturated non-aromatic 3- to 8-membered (preferably 5- or 6-membered) ring radical which contains one or more of same or different heteroatoms, or preferably one to four of same or different heteroatoms, selected from the group consisting of N, O and S. In one embodiment, the heterocycloalkyl includes one or more ring carbon atoms and/or heteroatoms, independently of each other, substituted with one or more of same or different substituents. In one embodiment, the heterocycloalkyl contains fused rings sharing a common carbon atom and/or a heteroatom. Non-limiting examples of the heterocycloalkyl include pyrrolidinyl, piperidinyl, quinuclidinyl, azetidinyl, morpholinyl, tetrahydrothiophenyl, tetrahydrofuranyl, dioxolanyl, dioxanyl and tetrahydropyranyl.

In one embodiment, the heterocycloalkenyl includes a partially saturated, nonaromatic 5- to 10-membered monocyclic, 8- to 12-membered bicyclic or 11- to 14-membered tricyclic ring having one or more of same or different heteroatoms selected from the group consisting of O, N and S. The unsaturated carbon or heteroatom may optionally be the point of attachment of the heterocycloalkenyl. In one embodiment, the heterocycloalkenyl includes one or more ring carbon atoms and/or heteroatoms, independently of each other, substituted with one or more of same or different substituents. In one embodiment, the heterocycloalkenyl contains fused rings sharing a common carbon atom and/or a heteroatom. Non-limiting examples of the heterocycloalkenyl include tetrahydropyridyl and dihydropyranyl.

In one embodiment, the aryl includes an aromatic monocyclic, bicyclic or tricyclic hydrocarbon ring, where one or more ring atoms capable of substitution may optionally be substituted, independently of each other, with one or more of same or different substituents. In one embodiment, the aryl contains fused rings sharing a common carbon atom. Non-limiting examples of the aryl include phenyl, naphthyl and anthracenyl.

In one embodiment, the heteroaryl includes an aromatic monocyclic, bicyclic or tricyclic ring having one or more heteroatoms selected from the group consisting of O, N and S. In one embodiment, the heteroaryl includes one or more ring carbon atoms and/or heteroatoms, independently of each other, substituted with one or more of same or different substituents. In one embodiment, the heteroaryl contains fused rings sharing a common carbon atom and/or a heteroatom. Non-limiting examples of the heteroaryl include pyridyl, 2,2'-bipyridyl, pyrazinyl, imidazolyl, oxazolyl, benzimidazolyl, phenanthrolinyl, quinolinyl, thiophenyl, indoyl, furanyl and pyrrolyl.

In one embodiment, the acyl has the formula $C(O)R^x$, wherein $R^x$ is alkyl. The alkyl included in the acyl preferably has from one to twelve carbon atoms, preferably from one to six carbon atoms, or more preferably from one to four carbon atoms.

It is to be appreciated that the substituent is not particularly limited, and may include any moiety that replaces one or more hydrogen atoms attached to a parent compound or structural feature. Non-limiting examples of the substituent include alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, and silyloxy.

Other anticancer ingredients or drugs which do not impair the functions of the compound of formula (I) may be added to the compound of formula (I), the composition or the medicament of the present invention. Such anticancer ingredients may include, but not limited to, an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine), an alkylating agent (including but not limited to busulfan, chlorambucil, cyclophosphamide, ifofamide, mechlorethamine, melphalan, and thiotepa), nonclassical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteriods (dexamethasone, prednisone, and methylprednisone), androgens such as fluoxymesterone and methyltestosterone), estrogens such as diethylstilbesterol, antiestrogens such as tamoxifen, LHRH analogues such as leuprolide, antiandrogens such as flutamdie, aminogluetethimide, megestrol acetate, and medroxyprogesterone, asparaginase, carmustine, lomustine, hexamethyl-melamine, dacarbazine, mitotane, streptozocin, cisplatin, carboplatin, levamasole, and leucovorin. The compound of the present invention can also be used in combination with enzyme therapy agents and immune system modulators such as an interferon, interleukin, tumor necrosis factor, macrophage colony-stimulating factor and colony stimulating factor.

The compound, composition or medicament of the present invention may be administered to a patient by any appropriate route which, for example, may include oral, parenteral, intravenous, intradermal, transdermal, mucosal, subcutaneous, and topical.

In aspect (1), the present invention provides a compound of formula (I):

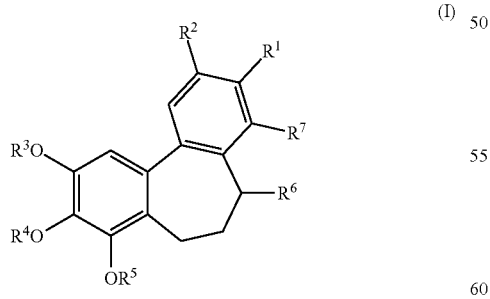

wherein: $R^1$ and $R^2$ are independently of each other H, OH, OR', C(O)OR', OP(O)(OH)$_2$ or a halogen atom, or $R^1$ and $R^2$ together with adjacent phenyl carbon atoms form a ring structure selected from the group consisting of cycloalkyl, cycloalkenyl, heterocycloalkyl or heterocycloalkenyl having one or more of N, O and S, aryl and heteroaryl having one or more of N, O and S, wherein the ring structure is optionally substituted; $R^3$ to $R^5$ are independently of each other H or R'; $R^6$ is R", NHR", O, OH or N$_3$; $R^7$ is H, OH or OR'; R' is optionally substituted aryl, optionally substituted alkyl, optionally substituted alkenyl or optionally substituted alkynyl; and R" is optionally substituted aryl, optionally substituted alkyl, optionally substituted alkenyl, optionally substituted alkynyl or optionally substituted acyl, or a salt, enantiomer or derivative thereof.

In aspect (2), the present invention provides the compound of aspect (1), wherein $R^1$ is H, OR', C(O)OR' or F and $R^2$ is H, OR' or C(O)OR', or $R^1$ and $R^2$ together with adjacent phenyl carbon atoms form heterocycloalkenyl or heteroaryl having one or more of N, O and S, and wherein R' is $C_1$-$C_4$ alkyl or benzyl.

In aspect (3), the present invention provides the compound of aspect (1) and/or aspect (2), wherein $R^6$ is NHR" and $R^7$ is H, and wherein R" is $C_1$-$C_4$ alkyl or acetyl.

In aspect (4), the present invention provides the compound of any one or more of aspects (1) to (3), wherein $R^1$ and $R^2$ are independently of each other H, OR' or C(O)OR', and $R^3$ to $R^5$ are R', and wherein R' is $C_1$-$C_4$ alkyl.

In aspect (5), the present invention provides the compound of any one or more of aspects (1) to (4), wherein the compound is

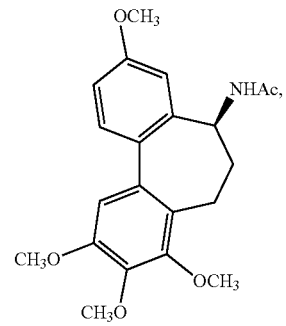

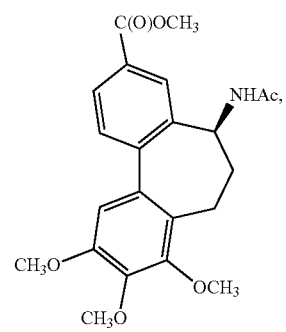

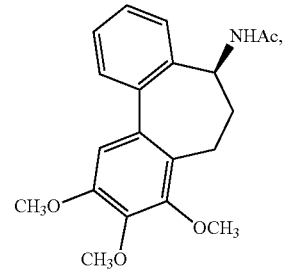

-continued

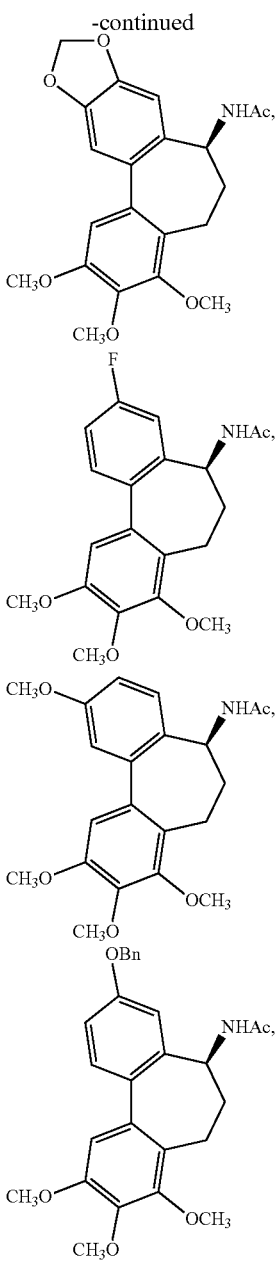

or a salt or derivative thereof, wherein Ac is C(O)CH₃ and Bn is benzyl.

In aspect (6), the present invention provides the compound of any one or more of aspects (1) to (5), wherein the compound is

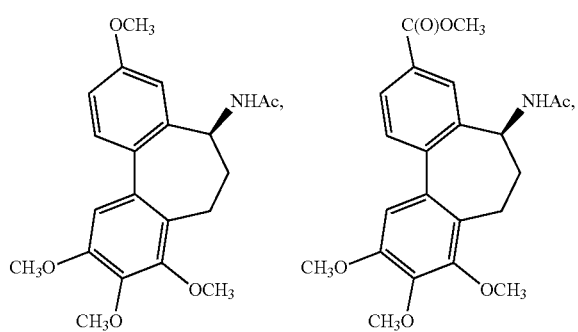

-continued

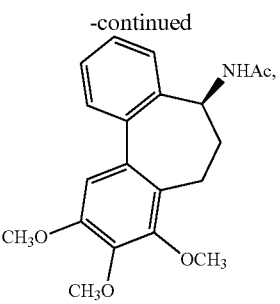

or a salt or derivative thereof, wherein Ac is C(O)CH₃.

In aspect (7), the present invention provides a compound of formula (II):

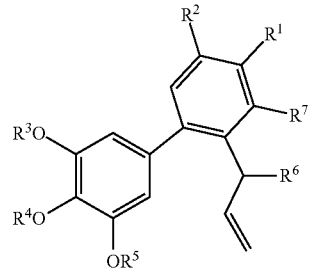

(II)

wherein: $R^1$ and $R^2$ are independently of each other H, OH, OR', C(O)OR', OP(O)(OH)$_2$ or a halogen atom, or $R^1$ and $R^2$ together with adjacent phenyl carbon atoms form a ring structure selected from the group consisting of cycloalkyl, cycloalkenyl, heterocycloalkyl or heterocycloalkenyl having one or more of N, O and S, aryl and heteroaryl having one or more of N, O and S, wherein the ring structure is optionally substituted; $R^3$ to $R^5$ are independently of each other H or R'; $R^6$ is O or OH; $R^7$ is H, OH or OR'; and R' is optionally substituted aryl, optionally substituted alkyl, optionally substituted alkenyl or optionally substituted alkynyl, or a salt, enantiomer or derivative thereof.

In aspect (8), the present invention provides the compound of aspect (7), wherein $R^1$ is H, OR', C(O)OR' or F and $R^2$ is H, OR' or C(O)OR', or $R^1$ and $R^2$ together with adjacent phenyl carbon atoms form heterocycloalkenyl or heteroaryl having one or more of N, O and S, and wherein R' is C$_1$-C$_4$ alkyl or benzyl.

In aspect (9), the present invention provides the compound of aspect (7) and/or aspect (8), wherein $R^1$ and $R^2$ are independently of each other H, OR' or C(O)OR', and $R^3$ to $R^5$ are R', and wherein R' is C$_1$-C$_4$ alkyl.

In aspect (10), the present invention provides the compound of any one or more of aspects (7) to (9), wherein the compound is

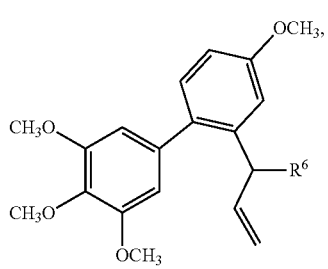

19

-continued

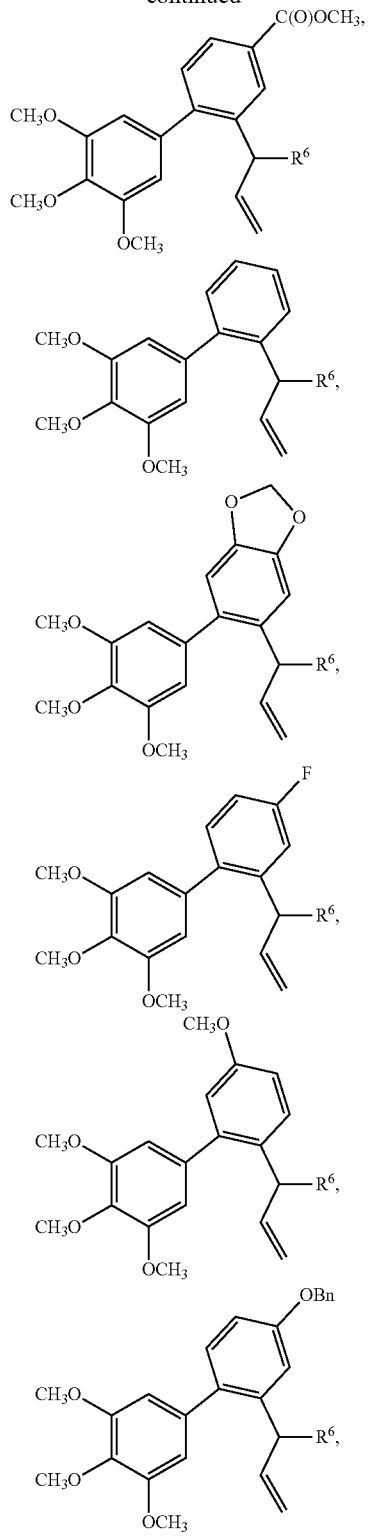

or a salt, enantiomer or derivative thereof, wherein Bn is benzyl, and wherein R⁶ is as defined in any one or more of aspects (7) to (9).

In aspect (11), the present invention provides the compound of any one or more of aspects (7) to (10), wherein the compound is

20

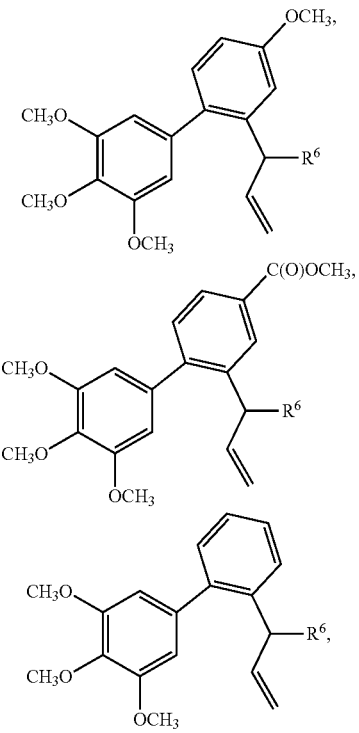

or a salt, enantiomer or derivative thereof, wherein R⁶ is as defined in any one or more of aspects (7) to (10).

In aspect (12), the present invention provides a method of producing a compound of formula (Ia), or a salt, enantiomer or derivative thereof:

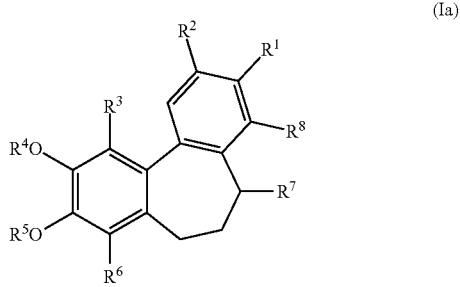

(Ia)

wherein: $R^1$ and $R^2$ are independently of each other H, OH, OR', C(O)OR', OP(O)(OH)$_2$ or a halogen atom, or $R^1$ and $R^2$ together with adjacent phenyl carbon atoms form a ring structure selected from the group consisting of cycloalkyl, cycloalkenyl, heterocycloalkyl or heterocycloalkenyl having one or more of N, O and S, aryl and heteroaryl having one or more of N, O and S, wherein the ring structure is optionally substituted; $R^3$, $R^6$ and $R^8$ are independently of each other H, OH or OR', wherein at least one of $R^3$ and $R^6$ is OR'; $R^4$ and $R^5$ are independently of each other H or R'; $R^7$ is R", NHR", O, OH or N$_3$; R' is optionally substituted aryl, optionally substituted alkyl, optionally substituted alkenyl or optionally substituted alkynyl; and R" is optionally substituted aryl, optionally substituted alkyl, optionally substituted alkenyl, optionally substituted alkynyl or optionally substituted acyl, the method comprising conducting a cyclization reaction of a compound of formula (III):

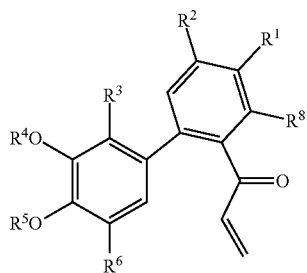

(III)

to obtain a compound of formula (IV):

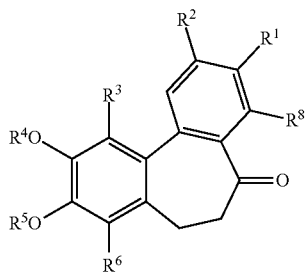

(IV)

wherein $R^1$ to $R^6$ and $R^8$ are as defined for the compound of formula (Ia), and wherein said conducting the cyclization reaction comprises conducting a Michael reaction in the presence of a Lewis acid.

In aspect (13), the present invention provides the method of aspect (12), wherein said conducting the Michael reaction comprises preparing a mixture containing the compound of formula (III), the Lewis acid and a solvent comprising chloroform, dichloromethane, nitrobenzene, acetonitrile, benzene, hexane, cyclohexane, toluene, chloroform, tetrahydrofuran, dimethylformamide or dimethyl sulfoxide, and optionally refluxing the mixture.

In aspect, (14), the present invention provides the method of aspect (12) and/or aspect (13), wherein the Lewis acid comprises one or more of $AlCl_3$, $AuCl_3$, $(CH_3)_2SAuCl$, $AgBF_4$, $FeCl_3$, $InCl_3$, $GaCl_3$, $SnCl_4$, $BF_3$—$O(CH_2CH_3)_2$ and trimethylsilyl trifluoromethanesulfonate.

In aspect (15), the present invention provides the method of any one or more of aspects (12) to (14), wherein $R^3$ is OR' and $R^6$ is H, and wherein the Lewis acid comprises $GaCl_3$ or $AlCl_3$ in an amount between 1 mol % and 800 mol % with respect to an amount of the compound of formula (III).

In aspect (16), the present invention provides the method of any one or more of aspects (12) to (15), wherein $R^3$ is H, and $R^6$ is OR', and wherein the Lewis acid comprises $BF_3$—$O(CH_2CH_3)_2$ in an amount between 1 mol % to 300 mol % with respect to an amount of the compound of formula (III).

In aspect (17), the present invention provides the method of any one or more of aspects (12) to (16), wherein the compound of formula (III) is obtained by reacting a compound of formula (V) with vinylmagnesium halide:

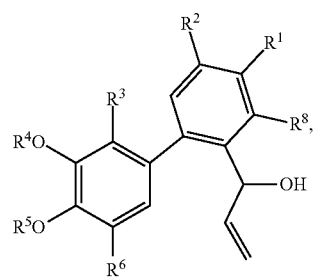

(V)

to obtain a compound of formula (VI):

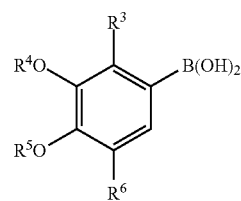

(VI)

and oxidizing the compound of formula (VI) to obtain the compound of formula (III), wherein $R^1$ to $R^6$ and $R^8$ are as defined in any one or more of aspects (12) to (16).

In aspect (18), the present invention provides the method of any one or more of aspects (12) to (17), wherein said oxidizing the compound of formula (VI) is conducted in the presence of $MnO_2$ or tetrapropylammonium perruthenate and N-Methylmorpholine N-oxide.

In aspect (19), the present invention provides the method of any one or more of aspects (12) to (18), wherein the compound of formula (V) is obtained by conducting a Suzuki-Miyaura coupling reaction between compounds of formulas (VII) and (VIII):

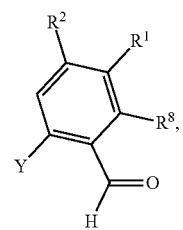

(VII)

(VIII)

wherein $R^1$ to $R^6$ and $R^8$ are as defined in any one or more of aspects (12) to (18), and Y is a halogen atom.

In aspect (20), the present invention provides the method of any one or more of aspects (12) to (19), the method further comprising reducing the compound of formula (IV) with 2-(3-nitrophenyl)-1,3,2-dioxaborolane-4R,5R-dicarboxylic acid to obtain a compound of formula (IX):

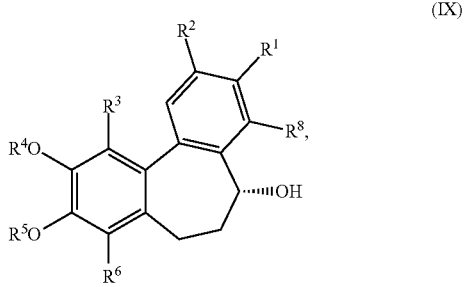

(IX)

reacting the compound of formula (IX) with an azide compound to obtain a compound of formula (X):

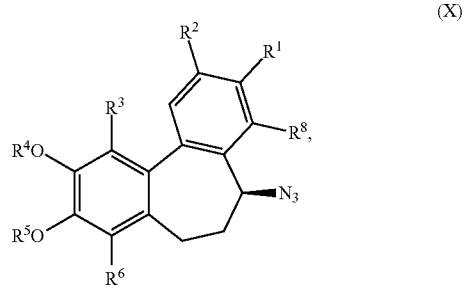

(X)

reducing the compound of formula (X) with hydrogen and a Lindlar catalyst to obtain a compound of formula (XI):

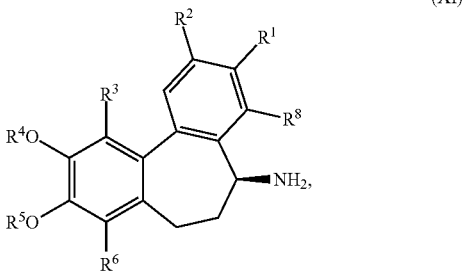

(XI)

and reacting the compound of formula (XI) with an acid anhydride compound to obtain the compound of formula (Ia), wherein $R^7$ is NHC(O)R''', R''' being alkyl, and wherein $R^1$ to $R^6$ and $R^8$ are as defined in any one or more of aspects (12) to (19).

In aspect (21), the present invention provides a method of treating or preventing a cancer, the method comprising administering a therapeutically effective amount of the compound of any one or more of aspects (1) to (6) to a patient.

In aspect (22), the present invention provides the method of aspect (21), wherein the cancer is pancreatic cancer or leukemia.

BRIEF DESCRIPTION OF THE DRAWINGS

FIG. 2 shows Scheme 2 for preparing compound 7a from compound 4a.

DETAILED DESCRIPTION OF THE PREFERRED EMBODIMENTS

The present invention relates to the synthesis of various cycloheptane-containing compounds, and more particularly application of cycloheptyne-$Co_2(CO)_6$ complexes, normally but not entirely derived by way of reactions of propargyl cation complexes. In this context, along with the methodology for ring synthesis, the applicant has proposed enantioselective syntheses of the known (−)-allocolchicine (synonym: (5S)-5H-5-(acetylamino)-6,7-dihydro-9,10,11-trimethoxydibenzo[a,c]cyclo-heptene-3-carboxylic acid, methyl ester) itself; the known NSC 51046 (synonyms: (S)—N-acetyl-O-methylcolchinol, NCME, N-[(5S)-6,7-dihydro-3,9,10,11-tetramethoxy-5H-dibenzo[a,c]cyclohepten-5-yl]acetamide); as well as 8,9,10-trimethoxy-isomer N-[(5S)-6,7-dihydro-3,8,9,10-tetramethoxy-5H-dibenzo[a,c]cyclohepten-5-yl]acetamide of Formula 1:

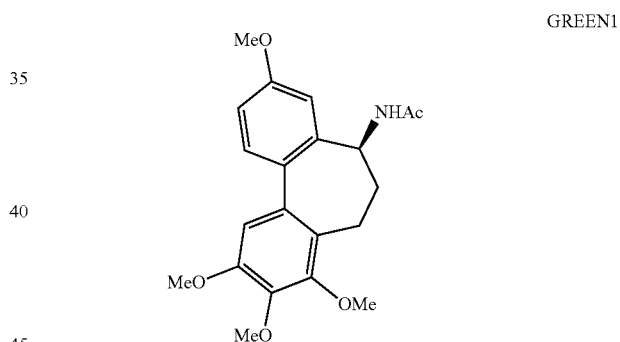

GREEN1

Not only was the compound of Formula 1 (also known as GREEN1) unknown, but due to its completely synthetic origin, it is the first and to date only of the allocolchicinoids with the 8,9,10-trimethoxy-substitution pattern reported.

It has been recognized that as a result of its novel substitution pattern compounds of Formula 1 may be promising for use in medicaments and/or antitumor agents. In particular, such compounds may not be cardiotoxic, and may provide a mechanism of action against pancreatic cancer and leukemia cell lines that is completely distinct from the conventional allocolicinoids. Further, without being bound by a particular theory, the mechanism for the compound of Formula 1 appears effective by way of pro-death autophagy.

Given the promising biological activity of compounds of Formula 1, applicant has developed novel methods of preparing the dibenzocycloheptane ring system and allocolchicines, which is distinct from cobalt/Nicholas reaction based chemistry.

Principal objects may be to at least partially achieve a critical seven membered-ring closure method which is catalytic in nature; which employs the cheapest possible reagents in the smallest possible amounts, and/or wherein other C ring substitution patterns would be possible.

In one possible approach, the generation of a biaryl alkenone as a substrate for conjugate addition chemistry is used. For the rearranged allocolchicine of interest and in particular, the compound of Formula 1 below:

Formula 1

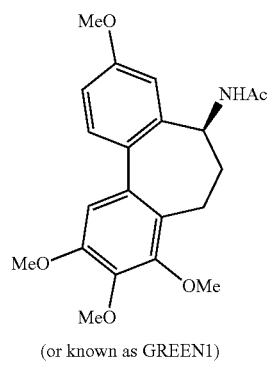

Figure 1:
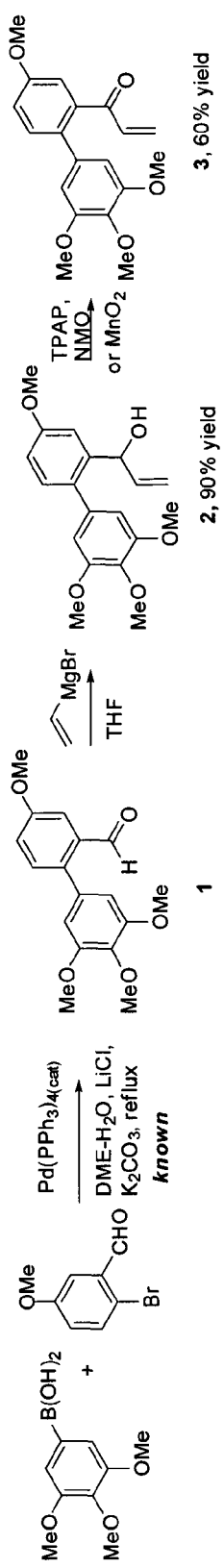
FIG. 1 shows Scheme 1 for preparing compound 3.

(or known as GREEN1)

the substrate was initially prepared from commercially available materials by way of Suzuki-Miyaura cross coupling (1) in accordance with the process of Scheme 1 shown in FIG. 1, followed by nucleophilic attack on the aldehyde by vinylmagnesium bromide, and oxidation of the resultant alcohol (2) to the ketone (3). The cross-coupling reaction product was first made in a cobalt mediated cyclization project based on known protocols. An addition reaction and subsequent oxidation reaction, however achieved new compounds and occurred as expected, and in good yield in accordance with the process of Scheme 1.

With the substrate of Formula (3) (FIG. 1) in hand, a number of protocols were investigated for the central Michael reaction type cyclization towards the seven-membered ring. Two complementary types of Lewis acids were investigated, including π-Lewis acids ($Au^{I/III}$, $Ag^{I}$) based and the more oxophilic Lewis acids. A complete list of results is included in Table 1.

The general features are as follows. Gold (III) Lewis acids enable the complete consumption of compound 3 to occur, but with the isolation of desired 4 only in low yield (with gross decomposition as the only by-product). Gold (I) systems in conjunctions with Ag(I) salts are able to cause reaction with approximately the same efficiency, but subsequent experiments have demonstrated that it is likely the added Ag(I) salt accomplishing the transformation; while there is evidence that these are proceeding catalytically, the yields realized are not sufficient. Oxophilic Lewis acids also gave some success, with indium (III) based Lewis acids showing transformation but no catalytic turnover, and gallium (III) Lewis acids so vigorous as to cause gross decomposition of the starting material. While preliminary results for $SnCl_4$ shows some hope that this could be optimized, there was greater early success with $BF_3$—$OEt_2$. Stoichiometric amounts of this Lewis acid gave good yields of target dibenzosuberone compound 4a. With experimentation, it was possible to get efficient cyclization to occur with 10 mol % $BF_3$—$OEt_2$ (see Table 1 below). Such an embodiment is believed to provide a commercially reasonable catalytic loading, and as $BF_3$—$OEt_2$ is the least expensive of all the Lewis acids investigated, it is believed to be preferred from a commercial perspective.

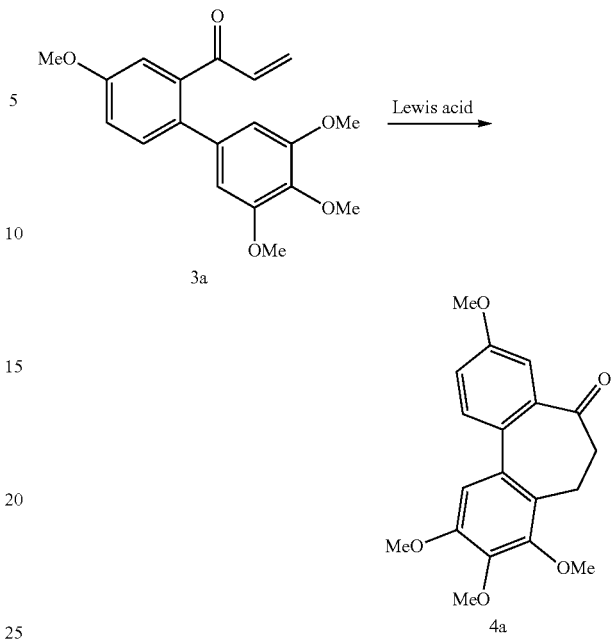

TABLE 1

Optimization of Dibenzocycloheptanone 4a Formation

| Lewis acid | Catalyst loading | Solvent | Conditions | Yield (4a)/conversion |
|---|---|---|---|---|
| $AuCl_3$ | 10 mol % | MeCN | RT, 3 h | 31% |
| $AuCl(SMe_2)$ + $AgBF_4$ | 25 mol % | $CH_2Cl_2$ | RT, 24 h | 28% |
| $AuCl(SMe_2)$ + $AgBF_4$ | 5 mol % | $CH_2Cl_2$ | RT, 24 h | 23% |
| $AgBF_4$ | 5 mol % | $CH_2Cl_2$ | RT, 24 h | 25% |
| $FeCl_3$ | 45 mol % | $CH_2Cl_2$ | RT, 4 h | 15% |
| $InCl_3$ | 25 mol % | $CH_2Cl_2$ | RT, 24 h | 23% |
| $InCl_3$ | 10 mol % | $CH_2Cl_2$ | RT, 24 h | 11% |
| $GaCl_3$ | 10 mol % | $CH_2Cl_2$ | RT, immediate | decomposition |
| $SnCl_4$ | 50 mol % | $CH_2Cl_2$ | RT, 3 h | 51% |
| $BF_3$—$OEt_2$ | 150 mol % | $CH_2Cl_2$ | RT, 24 h | 75% |
| $BF_3$—$OEt_2$ | 50 mol % | $CH_2Cl_2$ | RT, 24 h | 65% |
| $BF_3$—$OEt_2$ | 25 mol % | $CH_2Cl_2$ | RT, 24 h | 78% |
| $BF_3$—$OEt_2$ | 10 mol % | $CH_2Cl_2$ | RT, 24 h | 64% |
| $BF_3$—$OEt_2$ | 10 mol % | $CH_2Cl_2$ | −78° C.-RT, 3 h | 71% |
| $BF_3$—$OEt_2$ | 5 mol % | $CH_2Cl_2$ | RT, 24 h | 37% conversion |

From compound 4a, the completion of the synthesis of Formula 1 is achieved from the applicant's previous cobalt-based work described in (a) Djurdjevic, S.; Yang, F.; Green, J. R. *J. Org. Chem.* 2010, 75, 8241. (b) Djurdjevic, S.; Green, J. R. *Org. Lett.* 2007, 9, 5505, the disclosure of which is incorporated herein by reference in its entirety. Upon repetition of the procedure, improvements in the enantioselectivity of the process were made. In particular, as shown Scheme 2 illustrated in FIG. 2, TARB-$NO_2$ reduction afforded the alcohol 5 in highly enantiomerically enriched form. The Mitsunobu-type substitution by zinc azide gave the azide 6, whose reduction under Lindlar conditions, with subsequent N-acylation, gave 7a Formula 1. A single recrystallization afforded the material in >99% ee. As a result of this success delivery of 90 mg of 7a/Formula 1 has been achieved.

Figure 2:
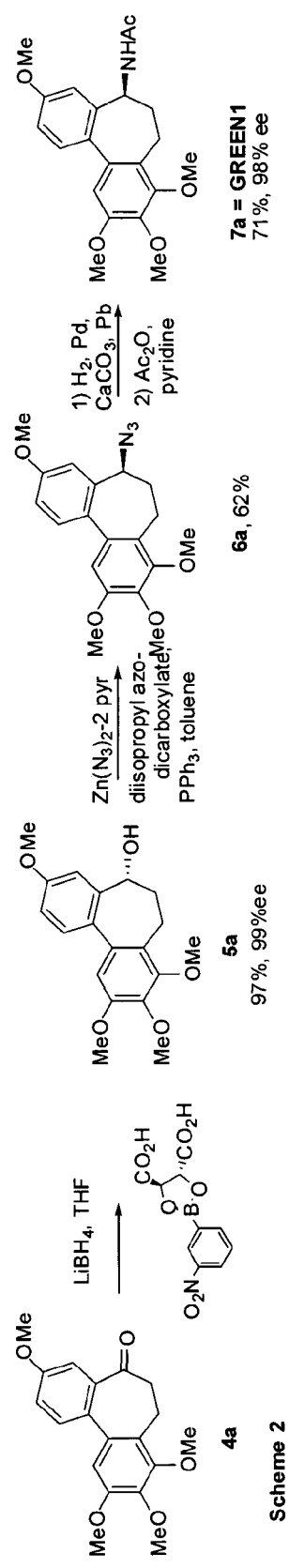

It is worth highlighting that during the development of this process, synthesis of compound 7a/Formula 1 (FIG. 2)

was shortened by five steps, from thirteen to eight from commercially available materials, making the synthesis much cheaper to carry out on a large scale.

In a subsequent embodiment, synthesis NSC 51046 (also referred to as the compound of Formula 14) having more well-known allocolchicine ring systems was undertaken. The catalytic access to such systems has been recognized as important. As well, comparative biological testing also provides a rationale for obtaining further amounts of this material.

Figure 3:
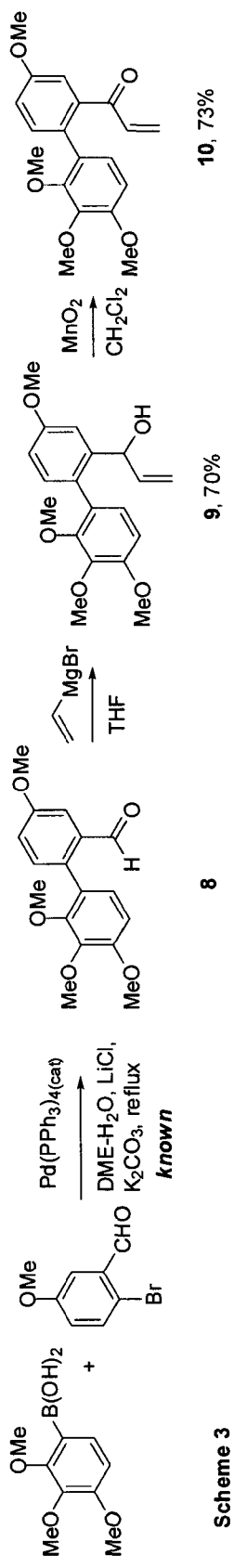
FIG. 3 shows Scheme 4 for preparing compound 10.

Preparation of the cyclization precursor is directly analogous to that described with reference to FIG. 2 in achieving compound 7a/Formula 1. As shown in FIG. 3, in accordance with Scheme 3, biaryl 8 is obtained by Suzuki-Miyaura coupling and which has been made previously, is similarly subjected to reaction with vinylmagnesium bromide. The resultant alcohol (9) is then oxidized to ketone 10.

With the critical substrate compound (10) in hand, a similar set of Lewis acid mediated Michael reaction protocols were investigated for the synthesis of dibenzocycloheptanone 11, bearing the 2,3,4-trimethoxyaryl substituent pattern of the conventionally known allocolchicines. While the complete list of results is summarized in Table 2, the salient features can be described as follows.

While BF$_3$—OEt$_2$ was found to be ideal for construction of the Formula 1 ring system, it is insufficient here. While the transformation occurs in reasonable yield with stoichiometric (full mole to mole equivalents) of BF$_3$—OEt$_2$, catalytic turnover does not occur (Table 2). With both gold(III) and In(III) Lewis acids, the slightest amount of turnover appears to occur, but with 30 mol % causing incomplete conversion and the expensive nature of these reagents, this is not acceptable. Iron(III) is similarly not catalytic, but in this case the gallium(III) catalyst is promising. By continual variation of test conditions, the applicant has achieved commercially reasonable yields of compound 11 (62% yield) at an adequately low loading (20 mol %). Chemically, these results are of the expected trend, as the arrangement of the methoxy groups makes this trimethoxybenzene ring less electron rich at the site that attacks as a nucleophile, and therefore a more aggressive set of reaction conditions should be required. Aesthetically, it is considered to be a near-optimized, but capable of improvement, with a target of 10 mol % catalyst loading being a goal.

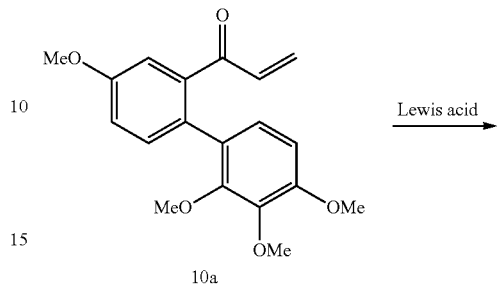

10a

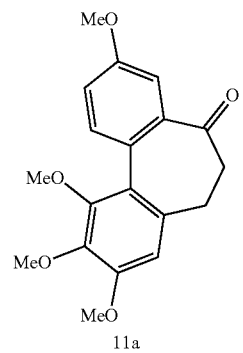

11a

TABLE 2

Optimization of Dibenzocycloheptanone 11a Formation

| Lewis acid | Catalyst loading | Solvent | Conditions | Yield (11)/conversion |
|---|---|---|---|---|
| AuCl$_3$ | 30 mol % | CH$_2$Cl$_2$ | RT, 24 h (left 3 d) | 50% conversion |
| FeCl$_3$ | 25 mol % | CH$_2$Cl$_2$ | RT, 24 h | 29% conversion |
| InCl$_3$ | 30 mol % | CH$_2$Cl$_2$ | RT, 24 h (left 4 d) | 45% conversion |
| TMSOTf | 40 mol % | CH$_2$Cl$_2$ | RT, 4 h | Unknown byproduct |
| BF$_3$—OEt$_2$ | 100 mol % | CH$_2$Cl$_2$ | RT, 48 h | 74% |
| BF$_3$—OEt$_2$ | 100 mol % | CHCl$_3$ | RT-reflux, 48 h | 66% |
| BF$_3$—OEt$_2$ | 20 mol % | CH$_2$Cl$_2$ | reflux, 24 h | no conversion |
| BF$_3$—OEt$_2$ | 20 + 30 mol % | CH$_2$Cl$_2$ | reflux, 48 h | 50% conversion |
| GaCl$_3$ | 50 mol % | CH$_2$Cl$_2$ | RT, 5 h | 72% |
| GaCl$_3$ | 25 mol % | | | 67% conversion |
| GaCl$_3$ | 20 mol % | CH$_2$Cl$_2$ | reflux, 2 d | 100% conv, 62% |
| GaCl$_3$ | 20 mol % | CH$_3$CN | reflux, 2 d | No conversion |

Figure 4:
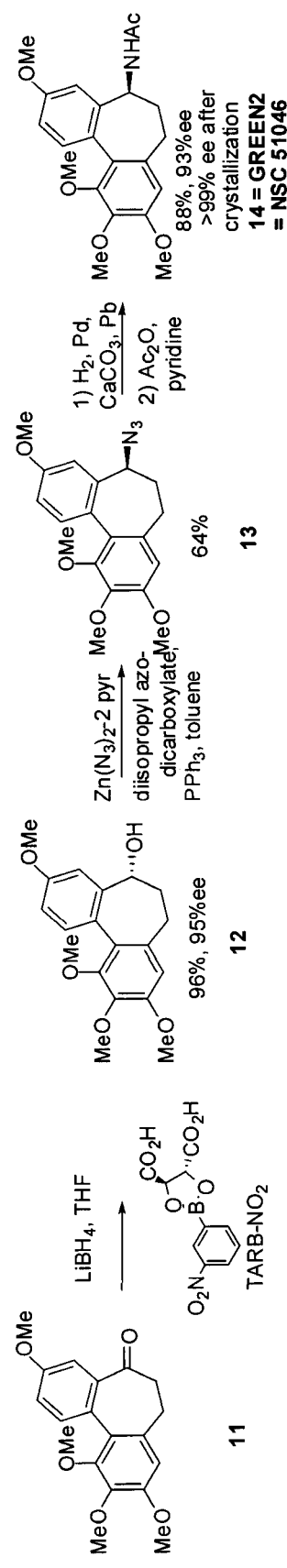
FIG. 4 shows Scheme 4 for preparing compound 14 from compound 11.

The conversion of 11a to the compound of Formula 14 is understood involving the analogous steps to the compound 7a/Formula 1 synthesis. As a result, as shown in FIG. 4 (Scheme 4), it may be summarized that optimization has shorted the total synthesis of the compound of Formula 14 by five steps (from thirteen to eight), with experimental results achieving 150 mg of material at the 11a stage.

With the Lewis acid catalyst mediated approach to the dibenzocycloheptanones and allocolchinoids worked out for Formula 1 and Formula 14, a generalized the methodology, particularly for the newer, 8,9,10-trimethoxy isomers may thus be understood. The precursors to these new A ring isomers of allocolchicines, (hereafter isoallocolchicines), are prepared by direct analogy to the successful chemistry of iso-NSC 51046 as follows:

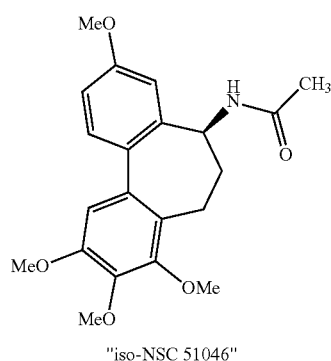

"iso-NSC 51046"

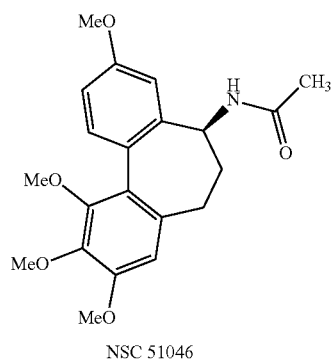

NSC 51046

Figure 5:
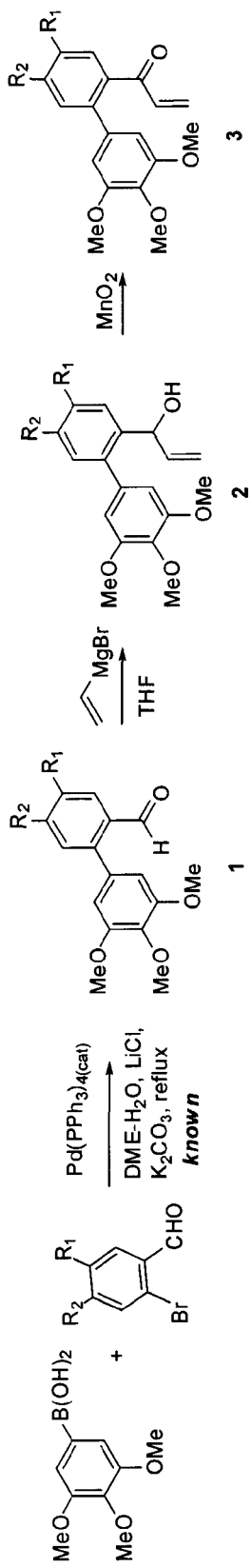
FIG. 5 shows Scheme 5 for preparing compound 3.

As shown with reference to Scheme 5 in FIG. 5, as before, Suzuki-Miyaura coupling of 3,4,5-trimethoxyphenylbroronic acid with the appropriate 2-bromobenzaldehyde gave the biaryls (1). These in turn underwent vinyl Grignard reagent addition to the aldehyde function (giving compound 2) of FIG. 5, and oxidation to give ketones 3. Five new examples are summarized in the table below.

TABLE 3

Preparation of Other Alkenone 3 Cyclization Precursors

| Entry | $R^1$ | $R^2$ | Yield 1 | Yield 2 | Yield 3 |
|---|---|---|---|---|---|
| b | H | H | 1b, 86% | 2b, 82% | 3b, 57% |
| c | CO₂Me | H | 1c, 76% | 2c, 84% | 3b, 62% |
| d | OCH₂O | | 1d, 40% | 2d, >95% | 3d, 72% |
| e | F | H | 1e, 95% | 2e, 90% | 3e, 71% |

TABLE 3-continued

Preparation of Other Alkenone 3 Cyclization Precursors

| Entry | $R^1$ | $R^2$ | Yield 1 | Yield 2 | Yield 3 |
|---|---|---|---|---|---|
| f | H | OMe | 1f, 79% | 2f, 80% | 3f, 76% brsm[a] |
| g | OBn | H | 1g, 91% | 2g, 80% | 3g, 70%, 81% brsm |

[a] brsm = yield based on recovered starting material

From the initial studies established in the iso-NSC 51046 (Formula 1) synthesis, conventional oxophilic Lewis acids (i.e., BF₃—OEt₂) have been shown to be superior than Lewis acids selective for alkene or alkyne π-systems; Consequently this approach is continued. For the targeted C ring system devoid of additional substitution (substrate 3b shown below), optimal yields of the cyclized compound 4b were realized with 5 mol % of BF₃—OEt₂ Lewis acid, and substantial conversion was realized at even 3 mol % catalyst loading. These are even lower catalyst amounts than required for iso-NSC 51046 (Formula 1) (10 mol %)

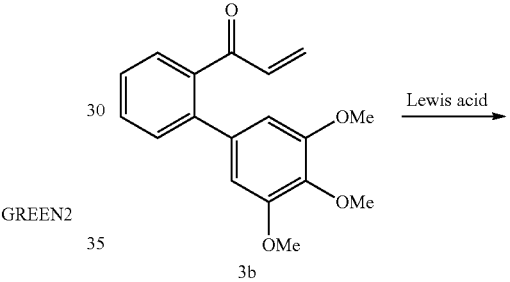

3b

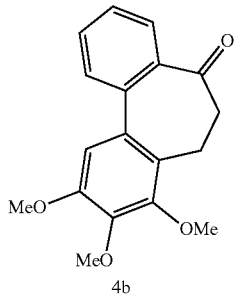

4b

TABLE 4

Optimization in the Synthesis of 4b

| Lewis acid | Catalyst loading | Solvent | Conditions | Yield (4)/conversion |
|---|---|---|---|---|
| BF₃—OEt₂ | 10 mol % | CH₂Cl₂ | 0°-RT, 12 h | 58% |
| BF₃—OEt₂ | 5 mol % | CH₂Cl₂ | 0°-RT, 12 h | 68% |
| BF₃—OEt₂ | 3 mol % | CH₂Cl₂ | 0°-RT, 12 h | 90% conv., 65% yield |

The ester-substituted substrate 3c is the A ring isomer of allocolchicine itself (to be called isoallocolchicine itself), and with 10 mol % BF₃—OEt₂ achieved good yields of cyclization as follows, much like iso-NSC 51046 (Formula 1). The 68% yield realized is quite respectable for this system.

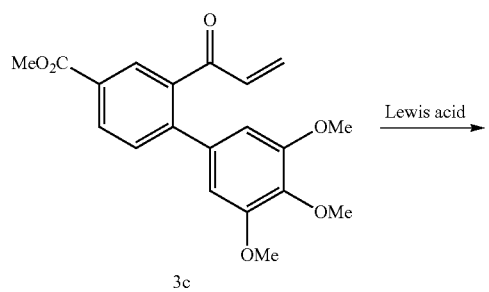

3c

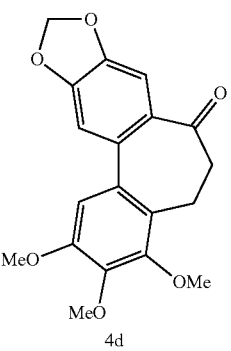

4d

TABLE 6

Optimization in the Synthesis of 4d

| Lewis acid | Catalyst loading | Solvent | Conditions | Yield (4)/ conversion |
|---|---|---|---|---|
| BF$_3$—OEt$_2$ | 25 mol % | CH$_2$Cl$_2$ | RT, 12 h | 55% |
| BF$_3$—OEt$_2$ | 5 mol % | CH$_2$Cl$_2$, $1.8 \times 10^{-3}$M | 3 d | 63% |

In a further embodiment, there is an interest in having at least one fluorine-substituted example of cyclization, given the omnipresence of fluorine-substituted drug candidates. Consequently the below illustrated reaction process 3e→4e, for example, may also prove commercially important. In the reaction shown, the yield of cyclization product was initially found to be low. As illustrated in Table 7, commercially reasonable yields of material were, however, obtained at the 5 mol % BF$_3$—OEt$_2$ loading level, whilst maintaining high-dilution conditions.

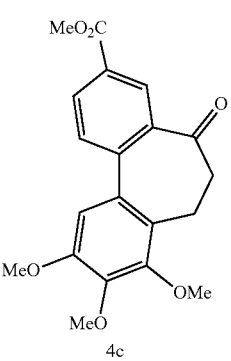

4c

TABLE 5

Optimization in the Synthesis of 4c

| Lewis acid | Catalyst loading | Solvent | Conditions | Yield (4)/ conversion |
|---|---|---|---|---|
| BF$_3$—OEt$_2$ | 25 mol % | CH$_2$Cl$_2$ | 0°-RT, 12 h | 71% |
| BF$_3$—OEt$_2$ | 10 mol % | CH$_2$Cl$_2$ | 0°-RT, 48 h | 68% |

Methylenedioxy-substituted 3d was also shown to behave very similarly to 3a and 3b, giving a reasonable yield of cyclization product 4d at 5 mol % BF$_3$—OEt$_2$ as follows and shown in Table 6.

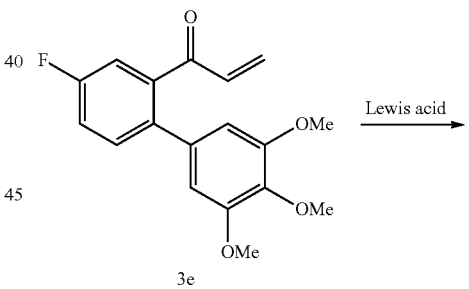

3e

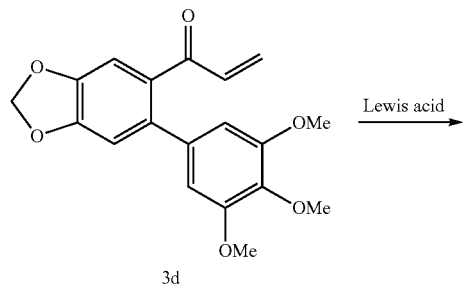

3d

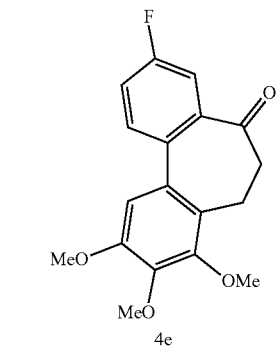

4e

TABLE 7

Optimization in the Synthesis of 4e

| Lewis acid | Catalyst loading | Solvent | Conditions | Yield (4)/ conversion |
|---|---|---|---|---|
| BF$_3$—OEt$_2$ | 10 mol % | CH$_2$Cl$_2$ | RT, 12 h | 35% |
| BF$_3$—OEt$_2$ | 5 mol % | CH$_2$Cl$_2$ | RT, 48 h | 43% |
| BF$_3$—OEt$_2$ | 2.5 mol % | CH$_2$Cl$_2$ | RT, 48 h | Incomplete conversion |
| BF$_3$—OEt$_2$ | 5 mol % | CH$_2$Cl$_2$, 1 × 10$^{-3}$M | RT, 48 h | 68% |

A substrate of the formula 3f with a C-5 substituted methoxy function, has also been found to provide a respectable yield of cyclization product with a 5 mol % BF$_3$—OEt$_2$ loading level, according to the criteria indicated in Table 8 and the reaction process.

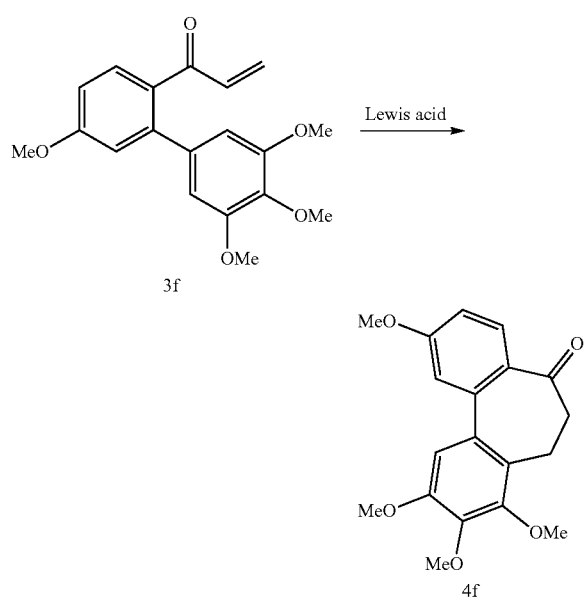

TABLE 8

Optimization in the Synthesis of 4f

| Lewis acid | Catalyst loading | Solvent | Conditions | Yield (4)/ conversion |
|---|---|---|---|---|
| BF$_3$—OEt$_2$ | 25 mol % | CH$_2$Cl$_2$ | RT, 2 × 10$^{-3}$M | 58% |
| BF$_3$—OEt$_2$ | 5 mol % | CH$_2$Cl$_2$ | RT, 2 × 10$^{-3}$M | 54% |
| BF$_3$—OEt$_2$ | 5 mol % | CH$_2$Cl$_2$ | RT, 1 × 10$^{-3}$M | 70% |

In further experimental studies, the C-4 benzyloxy substituted compound of formula 3g underwent ready cyclization with a 10 mol % BF$_3$—OEt$_2$ loading level, affording compound 4g in 83% yield. As shown below and overviewed in Table 9, the 5 mol % BF$_3$—OEt$_2$ loading level, while giving slower transformation, results in nearly the same amount of product.

TABLE 9

Optimization in the Synthesis of 4g

| Lewis acid | Catalyst loading | Solvent | Conditions | Yield (4)/ conversion |
|---|---|---|---|---|
| BF$_3$—OEt$_2$ | 10 mol % | CH$_2$Cl$_2$ [2.2 × 10$^{-3}$M] | 0° C.-RT, 12 h | 83% yield |
| BF$_3$—OEt$_2$ | 5 mol % | CH$_2$Cl$_2$ [1.9 × 10$^{-3}$M] | 0° C.-RT, 48 h | 81% yield |

Figure 6:
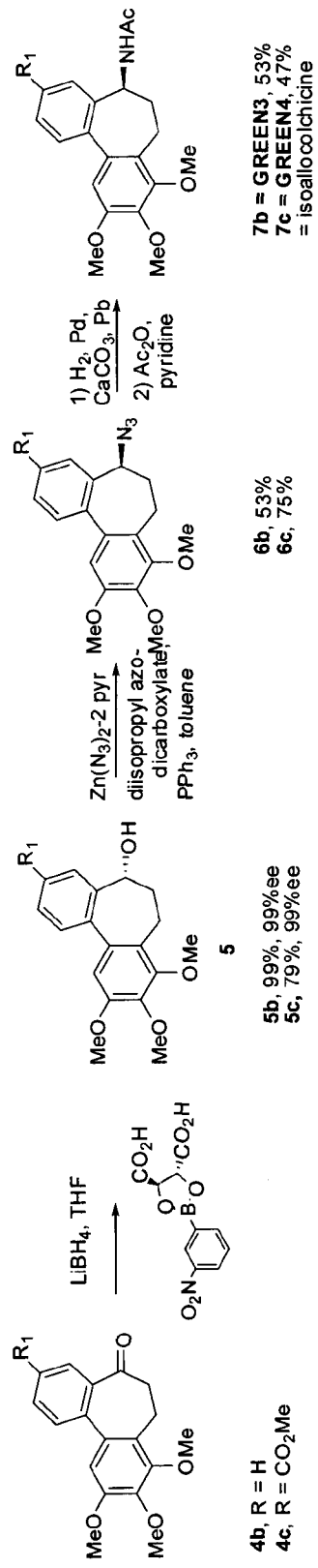
FIG. 6 shows Scheme 6 for preparing compounds 7b and 7c from compounds 4b and 4c, respectively.

Two of the aforementioned cyclization products compounds of Formula 4b, 4c have been converted into their respective isoallocolchicines successfully, applying the protocol for iso-NSC 51046 (Formula 1) as shown according to Scheme 6 shown in FIG. 6. In individual reactions, material has been pushed forward to get the target isoallocolchicines at the expense of truly optimized yields. As a result, some adjustment of chemical yields may be required. In each case, enantioselective reduction of the compound of 4 by LiBH$_4$/TARB-NO$_2$ (i.e. as shown in FIG. 2—Scheme 2) afforded the corresponding alcohols with excellent yield and enantioselectivity, see for example FIG. 6—Scheme 6/compound 5b, 99%, 99% ee; 5c, 79%, 99% ee). Mitsunobu-type substitution with zinc azide afforded the corresponding organic azides 6b (53% yield) and 6c (75% yield). Reduction of the azides 6b and 6c with Lindlar hydrogenation conditions, and acetylation of the resultant amine afforded the target isoallocolchicines 7b (52% yield) and 7c (47% yield) in enantiomerically pure form. The resulting two compounds (Formula 15/7b, 3 mg; and Formula 16/7c, 4.6 mg), which are new isoallocolchicines, have been delivered for preliminary evaluation.

An additional cyclization substrate bearing the 9,10,11-trimethoxyaryl substituent pattern of the conventionally known allocolchicines was demonstrated to be capable of cyclization to the corresponding dibenzocycloheptanone. In this case, according to the following reaction, and as shown in Table 10, from the compound of Formula (10b), greater than catalytic amounts of a Lewis acid (AlCl$_3$) were necessary for obtaining 11b.

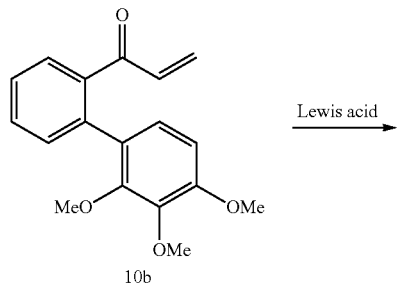

10b

TABLE 10

| | | Optimization in the Synthesis of 11b | | |
|---|---|---|---|---|
| Lewis acid | Catalyst loading | Solvent | Conditions | Yield (11)/ conversion |
| AlCl$_3$/ nitrobenzene | excess, 6 equiv | C$_6$H$_6$, 6 × 10$^{-3}$M | Reflux, 12 h | 52% |

Consequent, the use of catalytic amounts of Lewis acids on alkenone-substituted biaryls may be used as an efficient method for the synthesis of dibenzocycloheptanones with the 3',4',5'-trimethoxy-substitution pattern, and also shows applicability to the 2',3',4'-trimethoxy isomers. The resultant compounds have been demonstrated to be readily converted to the corresponding allocolchicnoids, of both the novel 3',4',5'-trimethoxy- and conventional 2',3',4'-trimethoxy-substitution patterns.

While the invention has been described with reference to preferred embodiments, the invention is not or intended by the applicant to be so limited. A person skilled in the art would readily recognize and incorporate various modifications, additional elements and/or different combinations of the described components consistent with the scope of the invention as described herein.

We claim:
1. A method of producing a compound of formula (Ia), or a salt or enantiomer thereof:

(Ia)

wherein:
R$^1$ and R$^2$ are independently of each other H, OH, OR', C(O)OR', OP(O)(OH)$_2$ or a halogen atom, or R$^1$ and R$^2$ together with adjacent phenyl carbon atoms form a ring structure selected from the group consisting of cycloalkyl, cycloalkenyl, heterocycloalkyl or heterocycloalkenyl having one or more of N, O and S, aryl and heteroaryl having one or more of N, O and S, wherein the ring structure is optionally substituted;
R$^3$, R$^6$ and R$^8$ are independently of each other H, OH or OR', wherein at least one of R$^3$ and R$^6$ is OR';
R$^4$ and R$^5$ are independently of each other H or R';
R$^7$ is R'', NHR'', O, OH, N$_3$ or NHC(O)R''';
R' is optionally substituted aryl, optionally substituted alkyl, optionally substituted alkenyl or optionally substituted alkynyl;
R'' is optionally substituted aryl, optionally substituted alkyl, optionally substituted alkenyl, optionally substituted alkynyl or optionally substituted acyl; and
R''' is alkyl,
the method comprising conducting a cyclization reaction of a compound of formula (III):

(III)

to obtain a compound of formula (IV):

(IV)

wherein R¹ to R⁶ and R⁸ are as defined for the compound of formula (Ia), and wherein said conducting the cyclization reaction comprises conducting a Michael reaction in the presence of a Lewis acid.

2. The method of claim 1, wherein said conducting the Michael reaction comprises preparing a mixture containing the compound of formula (III), the Lewis acid and one or more solvents selected from the group consisting of chloroform, dichloromethane, nitrobenzene, acetonitrile, benzene, hexane, cyclohexane, toluene, tetrahydrofuran, dimethylformamide and dimethyl sulfoxide, and optionally refluxing the mixture.

3. The method of claim 1, wherein the Lewis acid comprises one or more of $AlCl_3$, $AuCl_3$, $(CH_3)_2SAuCl$, $AgBF_4$, $FeCl_3$, $InCl_3$, $GaCl_3$, $SnCl_4$, $BF_3$—$O(CH_2CH_3)_2$ and trimethylsilyl trifluoromethanesulfonate.

4. The method of claim 1, wherein $R^3$ is OR' and $R^6$ is H, and wherein the Lewis acid comprises $GaCl_3$ or $AlCl_3$ in an amount between 1 mol % and 800 mol % with respect to an amount of the compound of formula (III).

5. The method of claim 1, wherein $R^3$ is H, and $R^6$ is OR', and wherein the Lewis acid comprises $BF_3$—$O(CH_2CH_3)_2$ in an amount between 1 mol % to 300 mol % with respect to an amount of the compound of formula (III).

6. The method of claim 1, wherein the compound of formula (III) is obtained by reacting a compound of formula (V) with vinylmagnesium halide:

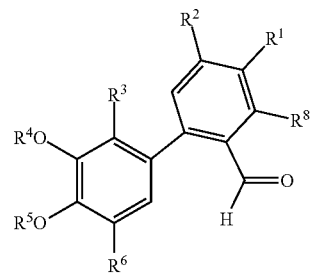

(V)

to obtain a compound of formula (VI):

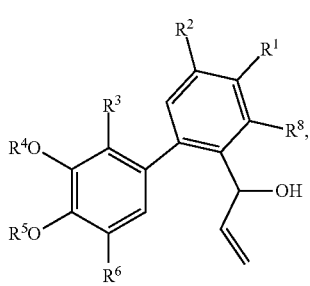

(VI)

and oxidizing the compound of formula (VI) to obtain the compound of formula (III), wherein R¹ to R⁶ and R⁸ are as defined in claim 1.

7. The method of claim 6, wherein said oxidizing the compound of formula (VI) is conducted in the presence of $MnO_2$ or tetrapropylammonium perruthenate and N-Methylmorpholine N-oxide.

8. The method of claim 6, wherein the compound of formula (V) is obtained by conducting a Suzuki-Miyaura coupling reaction between compounds of formulas (VII) and (VIII):

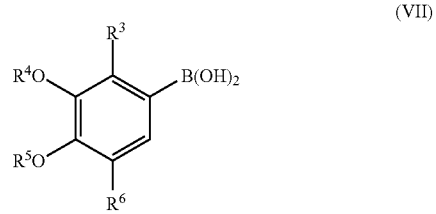

(VII)

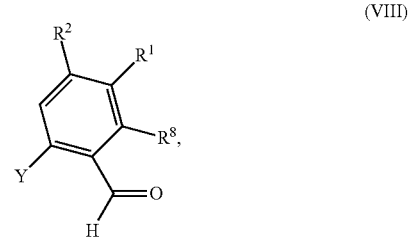

(VIII)

wherein R¹ to R⁶ and R⁸ are as defined in claim 6, and Y is a halogen atom.

9. The method of claim 1, the method further comprising reducing the compound of formula (IV) with 2-(3-nitrophenyl)-1,3,2-dioxaborolane-4R,5R-dicarboxylic acid to obtain a compound of formula (IX):

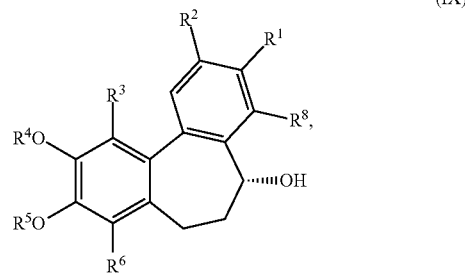

(IX)

reacting the compound of formula (IX) with an azide compound to obtain a compound of formula (X):

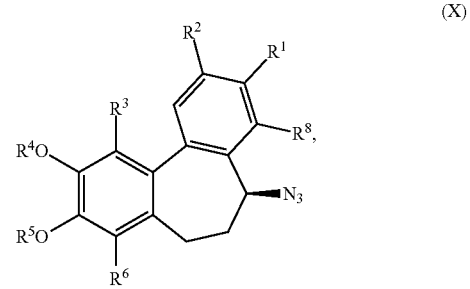

(X)

reducing the compound of formula (X) with hydrogen and a Lindlar catalyst to obtain a compound of formula (XI):

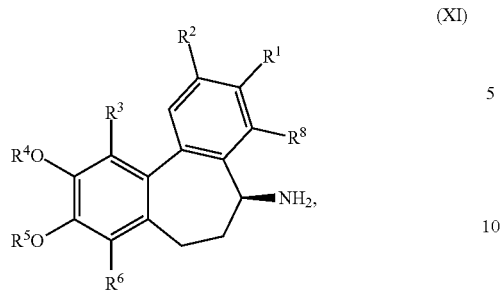
(XI)
and
reacting the compound of formula (XI) with an acid anhydride compound to obtain the compound of formula (Ia), wherein $R^7$ is NHC(O)R''', and wherein $R^1$ to $R^6$ and $R^8$ are as defined in claim 1.
* * * * *